United States Patent
Singer (10) Patent No.: US 9,135,381 B2
(45) Date of Patent: Sep. 15, 2015

(54) MODELING AND SIMULATION SYSTEM FOR OPTIMIZING PROSTHETIC HEART VALVE TREATMENT

(71) Applicant: STENOMICS, INC., Belmont, CA (US)

(72) Inventor: Michael A. Singer, Belmont, CA (US)

(73) Assignee: STENOMICS, INC., Belmont, CA (US)

( * ) Notice: Subject to any disclaimer, the term of this patent is extended or adjusted under 35 U.S.C. 154(b) by 0 days.

(21) Appl. No.: 14/264,544

(22) Filed: Apr. 29, 2014

(65) Prior Publication Data

US 2014/0336995 A1 Nov. 13, 2014

Related U.S. Application Data

(60) Provisional application No. 61/822,133, filed on May 10, 2013.

(51) Int. Cl.
| | | |
|---|---|---|
| *G06G 7/50* | (2006.01) | |
| *G06F 17/50* | (2006.01) | |
| *G09B 23/30* | (2006.01) | |
| *G06F 19/00* | (2011.01) | |

(52) U.S. Cl.
CPC .......... *G06F 17/5018* (2013.01); *G09B 23/303* (2013.01); *G06F 19/3437* (2013.01)

(58) Field of Classification Search
CPC .................................................. G06F 19/3437
USPC ............................................................ 703/9
See application file for complete search history.

(56) References Cited

U.S. PATENT DOCUMENTS

| | | | |
|---|---|---|---|
| 8,219,229 B2 | 7/2012 | Cao et al. | |
| 8,224,640 B2 | 7/2012 | Sharma et al. | |
| 8,682,626 B2 | 3/2014 | Ionasec et al. | |
| 2008/0319308 A1 | 12/2008 | Tang | |
| 2012/0022843 A1 | 1/2012 | Ionasec et al. | |
| 2012/0041739 A1* | 2/2012 | Taylor | 703/11 |
| 2012/0053918 A1* | 3/2012 | Taylor | 703/9 |
| 2012/0232386 A1 | 9/2012 | Mansi et al. | |
| 2012/0232853 A1 | 9/2012 | Voigt et al. | |

OTHER PUBLICATIONS

Marsden, "Optimal design and uncertainty quantification in blood flow simulation in congenital heart disease" p. 11 of FDA—NHIB—NSF Workshop on Computer Methods in Cardiovascular Device Design and Evaluation: The Integration of Nonclinical and Computer Models; 2010; 7 pages.*

(Continued)

*Primary Examiner* — Hugh Jones
(74) *Attorney, Agent, or Firm* — Dorsey & Whitney LLP (57) ABSTRACT

A computer-implemented method for simulating blood flow through a heart valve may first involve receiving patient-specific data, including imaging data related to the heart valve, an inflow tract of the heart valve and an outflow tract of the heart valve, and at least one clinically measured flow parameter. Next, the method may involve generating a digital model of the heart valve and the inflow and outflow tracts, based at least partially on the imaging data, discretizing the model, applying boundary conditions to a portion of the digital model that contains the heart valve and the inflow and outflow tracts, and initializing and solving mathematical equations of blood flow through the model to generate computerized flow parameters. Finally, the method may involve comparing the computerized flow parameters with the at least one clinically measured flow parameter.

24 Claims, 4 Drawing Sheets

(56) References Cited

OTHER PUBLICATIONS

Yoganathan et al.: Flow in Prosthetic Heart Valves: State-of-the-Art and Future Directions; Annals of Biomedical Engineering, vol. 33, No. 12, Dec. 2005; pp. 1689-1694.*
Chandran: Role of Computational Simulations in Heart Valve Dynamics and Design of Valvular Prostheses; Cardiovasc Eng Technol. Mar. 2010 ; 1(1): 18-38.*
PCT US 2013 057546, search report, Nov. 2013, 4 pages.*
Neal et al.: Current progress in patient-specific modeling; Briefings in Bioinformatics. vol. 11. No. 1; Advance Access published on Dec. 2, 2009; pp. 111-126.*
Enevoldsen, et al., "Computational Fluid Dynamics Using In Vivo Ultrasound Blood Flow Measurements", Ultrasonics Symposium (IUS), 2012 IEEE International, (Oct. 2012) pp. 1596-1599. (4 pages).
Haj-Ali, R. et al., "A general three-dimensional parametric geometry of the native aortic valve and root for biomechanical modeling", Journal of Biomechanics 45 (2012) pp. 2392-2397. (6 pages).
Marom, G. et al., "Numerical model of the aortic root and valve: Optimization of graft size and sinotubular junction to annulus ratio", J Thorac Cardiovasc Surg 2013. (6 pages).
Tan, F.P.P. et al., "Comparison of Aortic Flow Patterns Before and After Transcatheter Aortic Valve Inplantation", Cardiovascular Eng and Tech, vol. 3, No. 1, Mar. 2012, pp. 123-135. (13 pages).
Voigt, I. et al., "Patient-Specific Model of Left Heart Anatomy, Dynamics and Hemodynamics from 4D TEE: A First Validation Study", D.N. Metaxas and L. Axel (Eds.): FIMH 2011, LMCS 666, pp. 341-349 2011. (9 pages).

Votta, E. et al., "Toward patient-specific simulations of cardiac valves: State-of-the-art and future directions" Jorunal of Biomechanics 46 (2013) pp. 217-228. (12 pages).
Wang, Q. et al., "Patient-specific modeling of biomechanical interaction in transcatheter aortic valve deployment", Journal of Biomechanics 45 (2012) pp. 1965-1971. (7 pages).
Weinberg, E. et al., "Transient, Three-dimensional, Multiscale Simulations of the Human Aortic Valve", Cardiovasc Eng. Springer Science+Business Media, LLC 2007. (16 pages).
Wendell, David C. , "Incorporating the Aortic Valve into Computational Fluid Dynamics Models using Phase-Contrast MRI and Valve Tracking", (2011), Dissertations (2009-), Paper 170. http://epublications.marquette.edu/dissertations_mu/170. (176 pages).
PCT Search Report and Written Opinion, Application No. PCT/US2014/035914, Aug. 26, 2014, 18 pages.
Auricchio, F. et al., "*Simulation of Transcatheter Aortic Valve Implantation: A Patient-Specific Finite Element Approach*", Computer Methods in Biomechanics and Biomedical Engineering, E-pub. Feb. 13, 2013, vol. 17, No. 12, pp. 1347-1357. See abstract and pp. 1348-1352.
Dumont, K. et al., "*Validation of a Fluid-Structure Interaction Model of a Heart Valve Using the Dynamic Mesh Method in Fluent*", Computer Methods in Biomechanics and Biomedical Engineering, 2004, vol. 7, No. 3, pp. 139-146, DOI: 10.1080/10255840410001715222.
Le, Trung B. et al., "*Fluid-Structure Interaction of an Aortic Heart Valve Prosthesis Driven by an Animated Anatomic Left Ventricle*", Journal of Computational Physics, E-pub, Sep. 22, 2012, vol. 244, pp. 41-62. See abstract and pp. 42-51.

\* cited by examiner

MODELING AND SIMULATION SYSTEM FOR OPTIMIZING PROSTHETIC HEART VALVE TREATMENT

CROSS-REFERENCE TO RELATED APPLICATION

The present application claims priority to U.S. Provisional Patent Application No. 61/822,133, entitled "Modeling and Simulation System for Optimizing Prosthetic Heart Valve Treatment," filed on May 10, 2013. The full disclosures of all of the above-listed patent applications are hereby incorporated by reference herein.

FIELD

The present disclosure relates generally to the field of computer-aided modeling and simulation. More specifically, the disclosure relates to computer-based systems and methods for modeling cardiac anatomy and physiology for simulation, therapeutic, treatment, and/or diagnostic purposes.

BACKGROUND

Cardiovascular disease is the leading cause of death in the United States and claims the lives of more than 600,000 Americans each year. According to the World Health Organization, cardiovascular disease is the leading cause of death worldwide and claims the lives of approximately 7 million people per year. Further, according to the American Heart Association (AHA), more than five million Americans are diagnosed with heart valve disease, which is a form of cardiovascular disease, each year, and diseases of the aortic and mitral valves are the most prevalent. Combined, aortic and mitral valve diseases affect more than five percent of the U.S. population. Hence, it is clear that cardiovascular disease, and heart valve disease in particular, is a major health concern and impacts the lives of numerous people.

Aortic stenosis (AS), which is a form of aortic valve disease, is a ubiquitous and potentially life-threatening disease that impacts approximately 1.5 million people in the United States and is the third most common cardiovascular disorder in the western world. Aortic stenosis is a general term that characterizes the abnormal operation of the heart valve that separates the left ventricle from the ascending aorta, and AS may or may not be symptomatic. A stenosed aortic valve (AV) that does not open completely leads to abnormal blood flow through the valve and the aortic root. These abnormal flow patterns may lead to increased vascular resistance and insufficient downstream perfusion. In addition, an AV that does not close properly may lead to aortic regurgitation (AR), in which reverse flow traverses the AV during diastole when the valve is supposed to be closed completely.

Mitral regurgitation (MR), which is a form of mitral valve disease, is also a widespread and potentially life-threatening disease. In the United States, the occurrence of MR increases with age. In a study conducted in 2000, at least moderate MR was observed in 0.5% of participants aged 18 to 44 years and in 9.3% of participants aged 75 years or greater. In Europe, MR is the second most frequent valvular disease requiring surgery. Similar to aortic regurgitation, mitral regurgitation is a general term that characterizes the abnormal operation of the mitral valve, which is the valve that separates the left atrium from the left ventricle. When the mitral valve does not close properly, blood may leak from the ventricle into the atrium during contraction of the left ventricle and thereby decrease the pumping efficiency of the heart. In contrast to dysfunctional aortic valves, dysfunctional mitral valves may be repaired and may not require replacement.

The prognosis of patients with severe, untreated valvular heart disease is poor. In the case of AS, for example, clinical studies of untreated patients have demonstrated that survival rates are as low as 50% at two years and 20% at five years after the onset of symptoms. Further, acute mitral regurgitation is poorly tolerated and carries a poor prognosis in the absence of treatment. Therefore, it is evident that patients with symptomatic, severely diseased heart valves should seek treatment.

Accurate clinical diagnosis is instrumental in determining the severity and nature of heart valve disease. The American College of Cardiology (ACC) and the AHA have published medical guidelines that help characterize the clinical indications for valvular heart disease and the corresponding clinical treatments. In the context of AS, diagnosis is dependent on the quantitative values of various blood flow parameters as well as a visual inspection of the valve and its operation. The outcome of a patient examination may be a diagnosis of mild, moderate, severe or critical AS. Per society guidelines, only patients with symptomatic, severe or critical AS may be candidates for aortic valve replacement (AVR), which usually involves open heart surgery. Similarly, the ACC and AHA have published guidelines to help diagnose and treat diseases of the other three heart valves, and these diagnostic methods are based on analysis of medical images and characteristics of the blood flow.

Despite the apparent need for treatment, an increasing number of patients with symptomatic, severe AS are ineligible for open heart surgery and surgical AVR. Ineligibility for open chest surgery may be due to significant co-morbidities, such as high surgical risk, advanced age, history of heart disease or frailty. These patients have a poor prognosis and may benefit greatly from alternative therapies and treatments that do not require open chest surgery.

For patients deemed inoperable or who do not wish to undergo an invasive surgical operation, minimally invasive or transcatheter valve implantation may be an option for improving valvular function, alleviating symptoms, and improving quality of life. Transcatheter aortic valve replacement (TAVR), for example, is a minimally-invasive approach to replace the malfunctioning native aortic valve with a functional prosthetic valve. During a TAVR procedure, a prosthetic aortic valve is typically inserted via a catheter that is introduced via a femoral or transapical pathway. In contrast to surgical AVR, TAVR does not require a sternotomy (incision in the center of the chest that separates the chestbone to allow access to the heart), and a heart-lung machine is not needed because the heart is not stopped. Further, because the TAVR procedure is less invasive than surgical AVR, patients generally spend less time in the hospital, experience shorter recovery times, and may be less reluctant to undergo the procedure. Transcatheter valve implantation may also be an option to repair other heart valves such as the mitral or pulmonary valve. Alternatively, sutureless heart valves provide a minimally invasive mechanism for heart valve replacement.

Despite the apparent benefits of transcatheter valve replacement, there are serious clinical risks associated with the procedure. In the case of TAVR, for example, clinically significant post-procedural AR is a frequent problem and occurs in up to 50% of patients. Further, results from clinical trials suggest a linear relationship between the severity of post-procedural AR and 1- and 2-year mortality, and even mild AR may be associated with increased mortality. Therefore, to maximize the potential benefits of TAVR and minimize the long-term risks to patient well-being, AR should be minimized as much as possible. Other risks of transcatheter valve replacement, which are applicable to all percutaneously deployed heart valves, include stroke, vascular complications, improper deployment, obstruction of secondary vessels (e.g., coronary ostium), and valve migration.

Minimizing the risks of negative complications following transcatheter valve implantation requires careful pre-surgical planning and execution of the procedure. Valvular regurgitation in the presence of transcatheter aortic heart valves, for example, is often due to a large mean annulus size, valvular calcification, and/or improper sizing of the valve. Specifically, paravalvular regurgitation (i.e., undesired, reverse flow—or leakage—that occurs between the perimeter of the prosthetic valve and the aortic annulus) is a frequent occurrence with aortic valves and is often caused by improper valve sizing. In contrast to surgical valve replacement, wherein the surgeon may visually inspect the anatomic structure of the native valve and surrounding vasculature before implanting the prosthetic valve, transcatheter approaches currently rely on clinical imaging techniques (e.g., echocardiography, computed tomography, magnetic resonance imaging) for sizing, positioning, and deploying the prosthesis. These images may not provide accurate anatomic information suitable for precise planning and deployment of transcatheter valves, which may contribute to the relatively high incidence of complications (e.g., valvular regurgitation).

Two-dimensional images of inherently three-dimensional anatomy may provide inaccurate information for planning and executing transcatheter and minimally invasive procedures. In addition, imaging modalities with relatively low spatial resolution (e.g., ultrasound) may be unable to resolve anatomic structures that are critical for pre-surgical planning. In the context of TAVR, for example, relatively low resolution two-dimensional echocardiographic images are known to underestimate the size of the aortic annulus; the size of the annulus is used to select the size of the prosthetic valve. This underestimation of vascular dimension may lead to deployment of a relatively small prosthetic valve and thereby contribute to a high incidence of paravalvular regurgitation because the prosthetic valve is too small to fill the native annulus. In contrast, relatively high resolution two-dimensional computed tomography (CT) imaging is known to overestimate the size of the aortic annulus, and prosthetic valve sizing based on CT measurements often leads to a lower incidence of regurgitation. Hence, while proper sizing and pre-procedural planning of transcatheter and minimally invasive heart valve procedures is widely recognized as an essential component for maximizing clinical benefits, the means by which these heart valves are sized requires appreciable clinical judgment and is prone to error.

Therefore, it would be very desirable to have a system and method for accurately assessing the anatomic size and morphology of heart valves and the surrounding vasculature. Such a system and method would ideally facilitate proper selection, sizing, positioning, and pre-surgical planning of prosthetic heart valve procedures. Such systems should not expose patients to excessive risks.

DESCRIPTION OF RELATED ART

There are many academic and industrial research groups that use computer modeling and simulation to analyze flow through heart valves. Historically, valvular hemodynamic analyses have focused on the aortic heart valve and have employed methods of computational fluid dynamics (CFD) to provide detailed insight into the blood flow surrounding the aortic valve. These insights have then been used to facilitate the design and construction of heart valves with optimal or near optimal hemodynamic properties that maximize functionality and durability while minimizing the potentially fatal risks of valvular malfunction and adverse response.

In recent years, hemodynamic modeling of heart valves has included both surgically implanted and transcatheter prostheses, but the focus of most studies remains the aortic valve. With the rapidly expanding clinical deployment of transcatheter aortic heart valves, modeling and simulation has helped understand and characterize the unique hemodynamic challenges of transcatheter deployment in comparison to traditional surgical implantation of aortic valves. In particular, computer modeling has been used to quantify valvular regurgitation, downstream flow effects in the aortic arch, leaflet stresses, vascular response, and other characteristics of valvular implantation that impact device efficacy, robustness, durability, and longevity.

To date, all computer modeling and simulation studies of heart valves are focused on evaluating and improving prosthetic valve design and function.

BRIEF SUMMARY

In contrast to currently available systems and methods for computer modeling of heart valves, the embodiments described herein involve modeling and simulation systems and methods that may be used to facilitate the selection, sizing, deployment, and/or pre-surgical planning of prosthetic heart valves. The systems and methods may also be used to diagnose and assess diseased heart valves. Unlike currently available systems, the embodiments described herein are directed toward anatomic assessment for diagnostic and pre-surgical planning purposes (e.g., device selection, sizing, deployment), rather than device design and function. In various embodiments, the systems and methods may be applied to any one or more heart valves.

The modeling and simulation system described herein uses computer modeling to facilitate sizing and deployment of transcatheter heart valves (e.g., aortic valve, mitral valve). In addition to using anatomic and geometric data gathered through two- and/or three-dimensional imaging studies, the modeling and simulation system also incorporates physiologic (e.g., hemodynamic) data into the construction of an accurate anatomic model that serves as the basis for diagnosis and surgical planning/execution. Hemodynamic data, which are currently excluded from all valvular sizing methods, provide three-dimensional insight into local valvular morphology, which enables an accurate physiologic assessment for prosthesis sizing and deployment. The sizing and deployment data obtained from the modeling and simulation system provide physicians with clinically relevant information that enables informed decision-making and thereby reduces the possibilities of adverse clinical events (e.g., valvular regurgitation). In addition, the system also facilitates sensitivity and uncertainly analyses, thereby enabling the complete and accurate planning of heart valve implantation.

In one aspect, a computer-implemented method for simulating blood flow through a heart valve may first involve receiving patient-specific data, including imaging data related to the heart valve, an inflow tract of the heart valve and an outflow tract of the heart valve, and at least one clinically measured flow parameter. Next, the method may involve generating a digital model of the heart valve and the inflow and outflow tracts, based at least partially on the imaging data, discretizing the model, applying boundary conditions to a portion of the digital model that contains the heart valve and the inflow and outflow tracts, and initializing and solving mathematical equations of blood flow through the model to generate computerized flow parameters. Finally, the method may involve comparing the computerized flow parameters with the at least one clinically measured flow parameter. Optionally, the method may further involve adjusting the digital model after the comparison step. In some embodiments, the method may also involve, after adjusting the digital model, re-solving the mathematical equations to generate new computerized flow parameters. The method may further include comparing the new computerized flow parameters with the clinically measured flow parameters.

In some embodiments, the patient-specific data may be derived from only non-interventional data collection method(s) and/or minimally invasive data collection method(s). In some embodiments, generating the digital model may involve generating the model based at least partially on the imaging data and at least partially on the clinically measured flow parameter(s). Optionally, some embodiments may further involve performing a sensitivity analysis and/or an uncertainty analysis on the computerized flow parameters.

In various embodiments, the digital model may be used for diagnosing a disease state, assessing a disease state, determining a prognosis of a disease state, monitoring a disease state, planning a prosthetic heart valve implantation and/or performing a prosthetic heart valve implantation. The imaging data may be derived from any suitable imaging modality, such as but not limited to echocardiography, ultrasound, magnetic resonance imaging, x-ray, optical tomography and/or computed tomography. The clinically measured flow parameter(s) may be measured using any suitable modality, such as but not limited to Doppler echocardiography, catheterization and/or functional magnetic resonance.

In another aspect, a computer-implemented method for generating an anatomical model of a heart valve may include: receiving patient-specific imaging data of the heart valve and inflow and outflow tracts of the heart valve; generating a digital anatomical model of the heart valve and the inflow and outflow tracts, based at least partially on the imaging data; modeling blood flow through the digital model to generate a first set of computerized flow parameters; comparing the first set of computerized flow parameters with at least one clinically measured flow parameter; adjusting the digital model, based on the comparison of the first set of computerized flow parameters with the clinically measured flow parameters; modeling blood flow through the adjusted digital model to generate a second set of computerized flow parameters; and comparing the second set of computerized flow parameters with the at least one clinically measured flow parameter.

In some embodiments, the method may further involve, before adjusting the digital model, determining, based on the comparison of the first set of parameters with the clinically measured parameters, that the digital model is unacceptable. For example, determining that the digital anatomical model is unacceptable may involve determining that the first set of computerized flow parameters differs from the at least one clinically measured flow parameter by at least a predetermined threshold amount. In some embodiments, generating the first set of computerized flow parameters may involve: discretizing the digital model; applying boundary conditions to a portion of the digital model that contains the heart valve and the inflow and outflow tracts; and initializing and solving mathematical equations of blood flow through the digital model.

In some embodiments, the method may further involve, after the second comparing step: adjusting the adjusted digital anatomical model, based on the comparison of the second set of computerized flow parameters with the at least one clinically measured flow parameter, to generate a new adjusted digital anatomical model; modeling blood flow through the new adjusted digital model to generate a third set of computerized flow parameters; and comparing the third set of computerized flow parameters with the at least one clinically measured flow parameter. Some embodiments may involve repeating the adjusting, modeling and comparing steps until a desired level of agreement is reached between a most recently calculated set of computerized flow parameters and the at least one clinically measured flow parameter.

In another aspect, a system for generating an anatomical model of a heart valve may include at least one computer system configured to: receive patient-specific imaging data of the heart valve and inflow and outflow tracts of the heart valve; generate a first digital anatomical model of the heart valve and the inflow and outflow tracts, based at least partially on the imaging data; model blood flow through the first model to generate a first set of computerized flow parameters; compare the first set of computerized flow parameters with clinically measured flow parameters; adjust the first digital anatomical model, based on the comparison of the first set of computerized flow parameters with the clinically measured flow parameters, to generate a second digital anatomical model; model blood flow through the second model to generate a second set of computerized flow parameters; and compare the second set of computerized flow parameters with the clinically measured flow parameters.

Optionally, the computer system may be further configured to determine, before the adjusting step and based on the comparison of the first set of parameters with the clinically measured parameters, that the first digital anatomical model is unacceptable. For example, to determine that the first digital anatomical model is unacceptable, the at least one computer system may be configured to determine that the first set of flow parameters differs from the clinically measured flow parameters by at least a predetermined threshold amount. In some embodiments, the computer system may be further configured to repeat the determining, adjusting, modeling and comparing steps until a desired level of agreement is reached between a most recently calculated set of computerized flow parameters and the at least one clinically measured flow parameter.

In some embodiments, to generate the first set of computerized flow parameters, the computer system may be configured to: discretize the first model; apply boundary conditions to a portion of the first model that contains the heart valve and the inflow and outflow tracts; and initialize and solve mathematical equations of blood flow through the first model.

These and other aspects and embodiments will be described in further detail below, in reference to the attached drawing figures.

DETAILED DESCRIPTION

This disclosure describes computer modeling and simulation systems and methods that qualitatively and quantitatively characterize anatomic geometry of a heart valve and/or the corresponding inflow/outflow tracts of the heart. The various embodiments described herein may be applied to any single heart valve, a combination of multiple heart valves, and/or combinations of one or more heart valves and one or more coronary blood vessels. Although occasional references may be made to one specific heart valve, these specific references should not be interpreted as limiting the scope of this disclosure. For example, the aortic heart valve is occasionally used throughout this disclosure as a specific example of a prototypical heart valve. Illustration of the systems and methods via the example of the aortic heart valve, however, is not intended to limit the scope of the computer modeling and simulation systems and methods disclosed herein.

Figure 1:
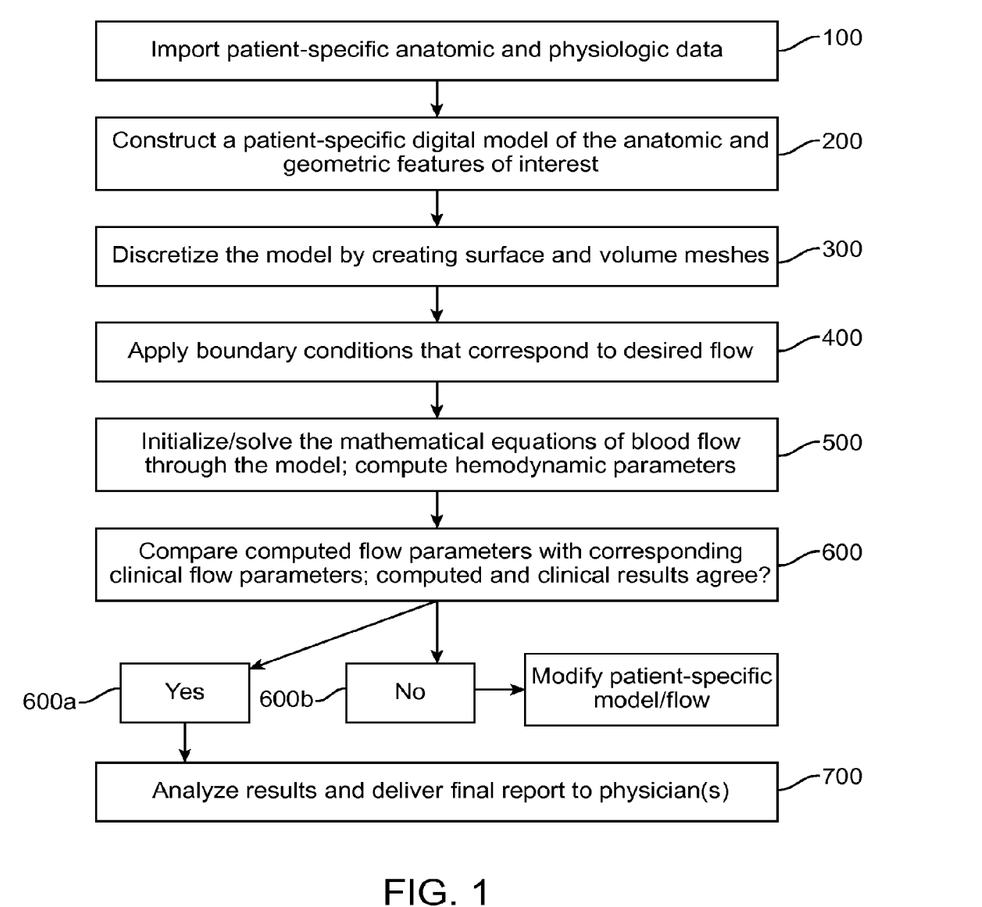
FIG. 1 is a flow diagram, outlining a method for modeling and simulation, according to one embodiment.

Referring to FIG. 1, one embodiment of a method for implementing a modeling and simulation system is illustrated. A first step of the method may involve importing or receiving patient-specific geometric, anatomic, physiologic, and/or hemodynamic data into the computer system 100. Typically, this patient-specific data includes at least some imaging data and at least one clinically measured flow parameter. In various embodiments, the imaging data and the clinically measured flow parameter(s) may be received by the system at the same time or at different times during the process. The system may receive data from any number and/or any type of patient-specific data collection source or modality. In some embodiments, all the data received may be data generated from non-invasive and/or minimally invasive modalities. Examples of imaging modalities from which data may be received include, but are not limited to, echocardiography, ultrasound, magnetic resonance imaging (MRI), x-ray, optical tomography such as optical coherence tomography (OCT) and computed tomography (CT). Examples of modalities which may be used for generating the received clinically measured flow parameter(s) include, but are not limited to, Doppler echocardiography, catheterization procedures, functional magnetic resonance, routine clinical tests (e.g., blood pressure, heart rate) and/or tests otherwise prescribed by physicians to diagnose abnormal function of the cardiac chambers or one or more heart valves.

Figure 2:
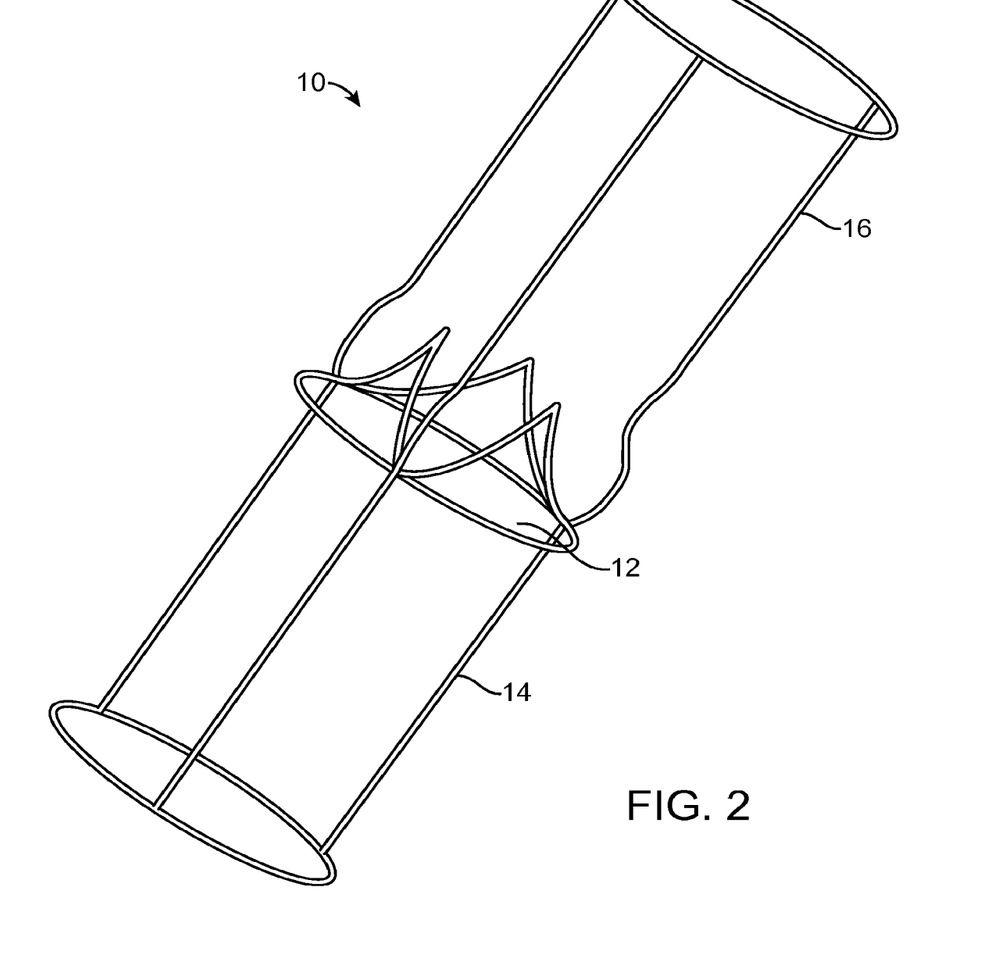
FIG. 2 is a perspective view of a simplified geometric model, based on patient-specific anatomic parameters, of the aortic valve and the surrounding cardiac inflow and outflow vessels, according to one embodiment.

The second step (FIG. 1) may involve constructing a (possibly parameterized) geometric model, using the imported/received data 200. A typical geometric model 10, as illustrated in FIG. 2, may be a multi-dimensional digital representation of the relevant patient anatomy, which may include at least one heart valve 12, at least a portion of an inflow vessel 14 (or "inflow tract"), and at least a portion of an outflow vessel 16 (or "outflow tract") of the corresponding valve 12. The model may also include one or more ventricles and/or atria of the heart or a portion thereof. The geometric model is created from patient-specific anatomical, geometric, physiologic, and/or hemodynamic data. In some embodiments, the model may be created 200 using exclusively imaging data. Alternatively, the model may be created 200 using imaging data and at least one clinically measured flow parameter. Imaging data may be obtained from any suitable diagnostic imaging exam(s), such as those listed above. Clinically measured flow parameters may be obtained from any suitable test(s), such as those listed above.

The model may also contain at least one inflow boundary and at least one outflow boundary through which blood flows in and out of the multi-dimensional model, respectively. These inflow and outflow boundaries may denote finite truncation of the digital model and may not be physically present in a patient. The digital geometric model may be created using methods of applied mathematics and image analysis, such as but not limited to image segmentation, machine learning, computer aided design, parametric curve fitting, and polynomial approximation. In various embodiments, a hybrid approach, which combines a collection of geometric modeling techniques, may also be used. The final, multi-dimensional model provides a digital surrogate that captures the relevant physical features of the anatomic topology under consideration and may contain one or more morphological simplifications that exploit the underlying geometric features of the patient-specific valvular and vascular system under consideration. Such simplifications may, for example, involve mathematical transformations (e.g., geometric smoothing) or the exclusion of anatomic structures (e.g., chordae tendineae of the mitral valve).

Referring again to FIG. 1, following the construction of the digital model 200, the modeling and simulation system may discretize the surface and volume of the model into a finite number of partitions 300. These individual and non-overlapping partitions, termed elements, facilitate the application and solution of the physical laws of motion that govern blood flow through the geometric model. The set of surface and volume elements used to discretize the model, collectively referred to as the computational mesh, transforms the continuous geometric model into a set of mesh points and edges, where each element point in the computational mesh has discrete x, y, and z spatial coordinates; each element edge is bounded by two mesh points and has a finite length.

Figure 3:
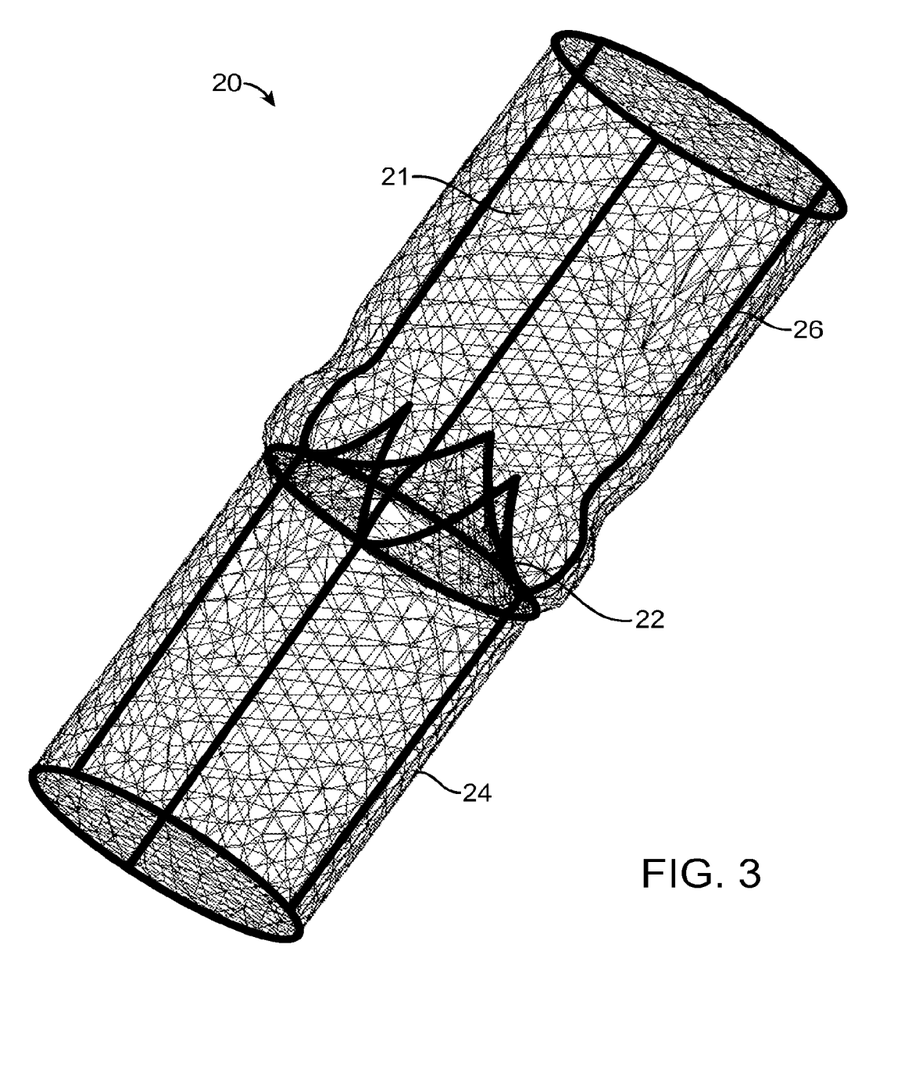
FIG. 3 is a perspective view of a simplified geometric model with the computational surface mesh, based on patient-specific anatomic parameters, of the aortic valve and the surrounding cardiac inflow and outflow vessels, according to one embodiment.
Figure 4A:
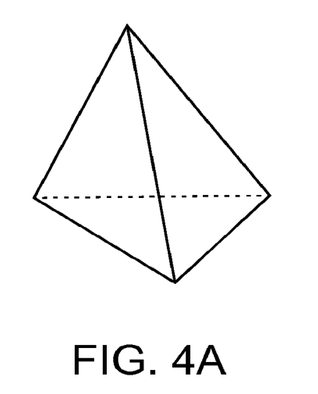
FIGS. 4A-4D are perspective views of representative polyhedra used to discretize the interior volume of the geometric model, according to one embodiment.
Figure 4B:
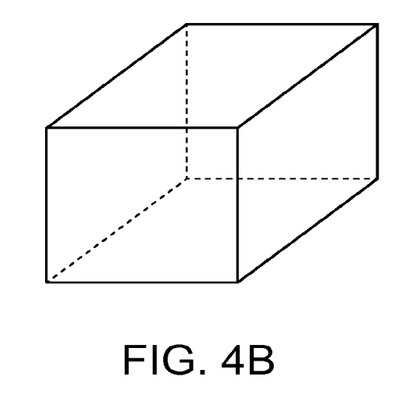
Figure 4C:
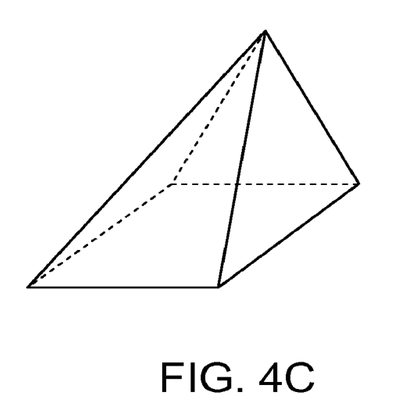
Figure 4D:
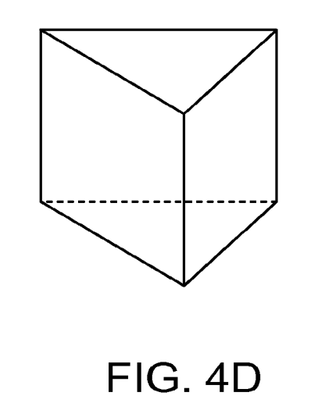

An illustration of a representative mesh 21 that discretizes the surface of a geometric model 20 is shown in FIG. 3. FIG. 3 is a perspective view of a geometric model 20, including an aortic valve 22, inflow tract 24 and outflow tract 26. This illustration of the model 20 is used to show the mesh 21.

Referring to FIGS. 4A-4D, the shape of the surface elements created by the modeling and simulation system may take the form of any closed polygon, but the surface mesh typically contains a collection of triangles, convex quadrilaterals or a combination thereof. Volume elements are created by the modeling and simulation system and are used to fill the interior of the model completely. Each volume element may take the form of any closed polyhedron, but the volume mesh (i.e., the set of volume elements) typically contains a collection of tetrahedra, hexahedra, wedges or a combination thereof (FIGS. 4A-4D). The surface and volume mesh densities, which determine the spatial resolution of the discrete model, may vary in space and time, as illustrated in FIG. 3. The local densities of the surface and volume meshes may depend on the complexity of the local topology of the underlying geometric model: more complex local topology may require higher spatial resolution, and therefore a higher mesh density, to resolve than local regions of less complex topology (e.g., see FIG. 3 (right) near the aortic valve 22).

The modeling and simulation system may use CFD to simulate blood flow through the discretized geometric model. Blood may be represented as a Newtonian or non-Newtonian fluid, and blood flow may be represented physically by the conservation of mass, momentum, and energy (or a combination thereof) and mathematically by the fluid flow equations (e.g., continuity, Navier-Stokes equations) with appropriate initial and boundary conditions; the boundary conditions may be constant or a function of time and/or space, and the boundary conditions may be different at different inflow/outflow surfaces. Initial and boundary conditions may be determined from empirical or heuristic relationships, clinical data, mathematical formulas or a combination thereof, and the model boundaries may be rigid or compliant or a combination thereof. The mathematical equations and corresponding initial and boundary conditions may be solved using conventional mathematical techniques, which include analytical or special functions, numerical methods (e.g., finite differences, finite volumes, finite elements, spectral methods), methods of machine learning or a hybrid approach that combines various aspects of the methods listed.

As a next step in the modeling and simulation method, and referring again to FIG. 1, the one or more boundary conditions may be applied to a discrete patient model 400. The boundary flow conditions may be obtained from patient-specific clinical measures (e.g., Doppler echocardiography, MRI), in which case they may be applied to the model in a manner that is consistent with clinical observations and measurements. In addition, inflow and outflow boundary conditions may be applied to compensate for underlying psychological or medical conditions such as pain, anxiety, fear, anemia, hyperthyroidism, left ventricular systolic dysfunction, left ventricular hypertrophy, hypertension or arterial-venous fistula, which may produce clinically misleading results, upon which medical diagnoses and treatments may be based.

Referencing FIG. 1 and following the initialization of the blood flow equations, the equations may be solved, and hemodynamic quantities may be computed, by the modeling and simulation system 500. The blood flow equations may be solved in a steady-state or time-dependent fashion; a hybrid approach that combines steady-state and time-dependent methods may also be used. Next, computed hemodynamic quantities may be compared with corresponding quantities obtained from clinical measurements, tests, and/or examinations (e.g., Doppler echocardiography, catheterization procedures, functional magnetic resonance or phase contrast MRI) 600. If the computed and clinically measured hemodynamic quantities are in satisfactory agreement 600a, then the results of the modeling and simulation system may be analyzed and information or a report may be delivered to a physician(s) or another medical professional 700. If the computed and clinically measured hemodynamic quantities are not in satisfactory agreement 600b, the patient-specific model may be modified in a manner thought to increase agreement between computed and clinical hemodynamic quantities, and a new computation may be performed with the modified model. Steps 300-600 may then be repeated until satisfactory agreement between computed and clinical data is obtained, and information or a report may be delivered to a physician(s) or another medical professional 700.

As an illustrative example of the embodiments described in 600, 600a, and 600b of FIG. 1, the clinically measured (via Doppler echocardiography, for example) peak velocity distal to the AV may be compared with the corresponding numerical value computed (via CFD) by the modeling and simulation system. If the computed and clinical velocities are agreeable to within a specified accuracy tolerance(s), then the geometric and hemodynamic models may be deemed accurate 600a, and information or a report that details the geometric and/or hemodynamic results may be delivered to a physician(s) or another medical professional 700. If, however, the computationally computed peak velocity and the clinically measured peak velocity fail to meet the specified accuracy tolerance(s) 600b, then the geometric and/or hemodynamic model may be adjusted and the flow may be recomputed via CFD. The new peak velocity distal to the AV that is computed with the new geometric and/or hemodynamic model may then be compared with the corresponding clinical velocity per 600 of FIG. 1. This iterative process of modifying the geometric and/or hemodynamic model, recomputing the flow, and comparing the computed and clinical velocities may be repeated until the computationally computed flow quantities and the clinically measured flow quantities are in satisfactory agreement.

After satisfactory agreement is achieved, the iterative process may be terminated, and information or a report that details the geometric and/or hemodynamic results may be delivered to a physician(s) or medical professional, per 700. In this illustrative example, the intent of adjusting the geometric and/or hemodynamic model is to maximize agreement between the computationally computed and clinically measured peak velocity distal to the AV, thereby ensuring the construction of an accurate geometric and hemodynamic model. In some embodiments, characterizing and understanding the similarities and differences between the clinically measured and/or derived results and the corresponding modeling and simulation system results may be used to adjust modeling parameters and maximize agreement between the clinically measured and/or derived results and those results numerically computed by the modeling and simulation system. These similarities and differences, as well as additional geometric and/or hemodynamic information provided by the modeling and simulation system, may also be used to guide clinical diagnoses and decision-making.

Output of each CFD analysis may include qualitative and/or quantitative geometric and hemodynamic information that may be computed directly from the CFD analysis and/or through one or more mechanisms of post-processing. These numerical results may be analyzed to reveal patient-specific anatomic, geometric, physiologic, and/or hemodynamic information that aid in the construction of an accurate and inclusive model at a single time or at a multitude of points in time. These qualitative and quantitative data may also be used to guide clinical decision-making and/or predictive information about disease state, progression or risk stratification.

Output data from the modeling and simulation system may be delivered to physicians or other medical professionals, who may use the data for clinical decision-making 700. Delivery of patient-specific information to medical professionals may occur via verbal discussions, written correspondence, electronic media or a combination thereof. These data may then be used by an individual physician or by a team of physicians to develop a complete, comprehensive, and accurate understanding of patient cardiac health and determine whether or not medical treatment is warranted. If medical treatment is warranted, then results from the modeling and simulation system may be used to guide clinical decision-making. Specific ways in which output from the modeling and simulation system may be incorporated into the clinical management of cardiac patients include, but are not limited to: (1) analysis of heart valve operation, including, for example, diagnosing the severity, functional significance, mechanism, and clinical response to abnormal heart valve operation; (2) pre-surgical planning of heart valve procedures, including, for example, patient-specific selection, sizing, deployment mechanisms, and positioning of prosthetic heart valves for surgical, minimally invasive, transcatheter or valve-in-valve treatments; (3) post-surgical assessment of heart valve procedures, including, for example, regurgitation, gradients, velocities, pressures, placements or efficacy; and (4) patient monitoring and/or follow-up. This list of potential uses for the systems and methods described herein is for example purposed only, and the list is not intended to be exhaustive.

The modeling and simulation system provides a virtual framework for conducting patient-specific sensitivity analyses. Such analyses may assess the relative impacts of anatomic and/or physiologic changes to the underlying anatomy and/or hemodynamic state of a patient. These state changes may then be assessed for functional and clinical significance, thereby estimating patient response to therapy, disease progression, and/or patient-specific risk stratification. Sensitivity analyses may be performed, for example, by coupling the modeling and simulation system with Monte Carlo and/or adjoint-based numerical methods that interact closely with the modeling and simulation system described above (FIG. 1). These numerical methods may be derivative-based or derivative-free and may enable numerous anatomic, geometric, physiologic, and/or hemodynamic scenarios to run in a virtual environment without exposing patients to any medical risks. Results from the plethora of simulations conducted during a sensitivity analysis may be aggregated and presented to a medical professional to aid with clinical decision-making Results from sensitivity analyses may also be used in conjunction with uncertainty analyses to assess global and/or local uncertainties of anatomic, geometric, physiologic, and/or hemodynamic results produced by the modeling and simulation system. Uncertainty analysis may also be used to assess the clinical impact or significance of variability or unknown parameters associated with device(s) that may be deployed during treatment (e.g., manufacturing tolerances).

The modeling and simulation system may enable planning of heart valve replacement therapy and the selection of optimal valve deployment. In particular, executing the modeling and simulation system described herein may provide an accurate assessment of anatomic, geometric, physiologic, and/or hemodynamic considerations for valvular deployment and function, e.g., valve type, size, mechanism, angle and/or the like. Hence, the modeling and simulation systems and methods may provide a complete framework that facilitates the accurate and complete anatomic and physiologic assessment of heart valves and their corresponding inflow/outflow tracts. This information may be used by medical professionals to guide clinical decisions regarding patient treatment of heart valve disease as to maximize the benefits to each patient.

Although the foregoing description is intended to be complete, any of a number of acceptable additions, subtractions or alterations to the described systems and methods may be made, without departing from the scope of the invention. For example, various method steps may be eliminated or performed in different order. Therefore, this description is provided for exemplary purposes, and should not be interpreted as limiting the scope of the invention.

What is claimed is:

1. A computer-implemented method for simulating blood flow through a native heart valve, the method comprising:
   receiving patient-specific imaging data related to the native heart valve, an inflow tract of the native heart valve and an outflow tract of the native heart valve;
   receiving at least one patient-specific clinically measured flow parameter related to blood flow through the native heart valve and the inflow and outflow tracts;
   generating a rigid-walled geometric model of the native heart valve and the inflow and outflow tracts at a single point in time, based at least partially on the imaging data, the rigid-walled geometric model having modeling parameters;
   discretizing the rigid-walled geometric model;
   applying boundary conditions, corresponding to desired flow, to a portion of the rigid-walled geometric model that contains the native heart valve and the inflow and outflow tracts, wherein applying the boundary conditions comprises selecting boundary conditions based at least partially on patient-specific clinical measurements;
   initializing and solving mathematical equations of blood flow through the rigid-walled geometric model to generate a first set of computerized flow parameters by simulating blood flow through the model while the model characterizes physical features of an anatomic topology of the native heart valve and inflow and outflow tracts at the single point in time;
   comparing the first set of computerized flow parameters with the at least one clinically measured flow parameter;
   adjusting at least one of the modeling parameters of the rigid-walled geometric model based on the comparing of the first set of computerized flow parameters with the at least one clinically measured flow parameter, wherein the at least one of the modeling parameters comprises at least one of the physical features of an anatomic topology;
   re-solving the mathematical equations to generate a second set of computerized flow parameters that agrees more closely with the at least one clinically measured flow parameter than the first set of computerized flow parameters agrees with the at least one clinically measured flow parameter, the closer agreement indicating a more accurate rigid-walled geometric model; and
   repeating the comparing, adjusting and re-solving steps until a desired level of agreement is reached between a most recently calculated set of computerized flow parameters and the at least one clinically measured flow parameter.

2. A method as in claim 1, wherein selecting the boundary conditions comprises selecting inflow and outflow boundary conditions that compensate for at least one underlying psychological condition or medical condition, wherein the at least one underlying psychological condition or medical condition is selected from the group consisting of pain, anxiety, fear, anemia, hyperthyroidism, left ventricular systolic dysfunction, left ventricular hypertrophy, hypertension and arterial-venous fistula.

3. A method as in claim 1, wherein receiving the patient-specific imaging data comprises receiving at least one of non-interventionally generated data or minimally invasively generated data.

4. A method as in claim 1, wherein generating the rigid-walled geometric model comprises generating the rigid-walled geometric model based at least partially on the imaging data and at least partially on the at least one clinically measured flow parameter.

5. A method as in claim 1, further comprising performing at least one of a sensitivity analysis or an uncertainty analysis on the first and second sets of computerized flow parameters.

6. A method as in claim 1, further comprising using the rigid-walled geometric model for at least one of diagnosing a disease state, assessing a disease state, determining a prognosis of a disease state, monitoring a disease state, planning a prosthetic heart valve implantation or performing a prosthetic heart valve implantation.

7. A method as in claim 1, wherein receiving the patient-specific imaging data comprises receiving the imaging data from an imaging modality selected from the group consisting of echocardiography, ultrasound, magnetic resonance imaging, x-ray, optical tomography and computed tomography.

8. A method as in claim 1, wherein receiving the at least one clinically measured flow parameter comprises receiving a parameter selected from the group consisting of a Doppler echocardiograph, a catheterization and a functional magnetic resonance image.

9. A computer-implemented method for generating a rigid-walled geometric model of a native heart valve, the method comprising:
  receiving patient-specific imaging data of the native heart valve and inflow and outflow tracts of the native heart valve;
  generating a rigid-walled geometric model of the native heart valve and the inflow and outflow tracts at a single point in time, based at least partially on the imaging data, the geometric model having modeling parameters and model boundaries representing physical features of an anatomic topology of the native heart valve and inflow and outflow tracts at the single point in time;
  modeling blood flow through the rigid-walled geometric model to generate a first set of computerized flow parameters, wherein generating the first set of computerized flow parameters comprises applying boundary conditions, corresponding to desired flow, to a portion of the rigid-walled geometric model that contains the native heart valve and the inflow and outflow tracts, and wherein applying the boundary conditions comprises selecting boundary conditions based at least partially on patient-specific clinical measurements;
  comparing the first set of computerized flow parameters with at least one clinically measured flow parameter;
  adjusting at least one of the modeling parameters of the rigid-walled geometric model, based on the comparison of the first set of computerized flow parameters with the clinically measured flow parameters, wherein the at least one of the modeling parameters comprises at least one of the physical features;
  modeling blood flow through the adjusted rigid-walled geometric model to generate a second set of computerized flow parameters that agrees more closely with the at least one clinically measured flow parameter than the first set of computerized flow parameters agrees with the at least one clinically measured flow parameter, the closer agreement indicating a more accurate rigid-walled geometric model;
  comparing the second set of computerized flow parameters with the at least one clinically measured flow parameter; and
  repeating the adjusting, modeling and comparing steps until a desired level of agreement is reached between a most recently calculated set of computerized flow parameters and the at least one clinically measured flow parameter.

10. A method as in claim 9, further comprising, before adjusting the at least one modeling parameter of the geometric model, determining, based on the comparison of the first set of parameters with the clinically measured parameters, that the geometric model is unacceptable.

11. A method as in claim 10, wherein determining that the geometric model is unacceptable comprises determining that the first set of computerized flow parameters differs from the at least one clinically measured flow parameter by at least a predetermined threshold amount.

12. A method as in claim 9, wherein generating the first set of computerized flow parameters further comprises:
  discretizing the rigid-walled geometric model; and
  initializing and solving mathematical equations of blood flow through the rigid-walled geometric model.

13. A method as in claim 9, wherein receiving the patient-specific imaging data comprises receiving at least one of non-interventionally generated data or minimally invasively generated data.

14. A method as in claim 9, wherein receiving the patient-specific imaging data comprises receiving the imaging data from an imaging modality selected from the group consisting of echocardiography, ultrasound, magnetic resonance imaging, x-ray, optical tomography and computed tomography.

15. A method as in claim 9, wherein receiving the at least one clinically measured flow parameter comprises receiving a parameter selected from the group consisting of a Doppler echocardiograph, a catheterization and a functional magnetic resonance image.

16. A method as in claim 9, further comprising performing at least one of a sensitivity analysis or an uncertainty analysis on at least one of the first set or the second set of computerized flow parameters.

17. A method as in claim 9, further comprising using the adjusted geometric model for at least one of diagnosing a disease state, assessing a disease state, determining a prognosis of a disease state, monitoring a disease state, planning a prosthetic heart valve implantation or performing a prosthetic heart valve implantation.

18. A method as in claim 9, wherein the repeating step comprises:
  adjusting the adjusted geometric model, based on the comparison of the second set of computerized flow parameters with the at least one clinically measured flow parameter, to generate a new adjusted geometric model;
  modeling blood flow through the new adjusted geometric model to generate a third set of computerized flow parameters; and
  comparing the third set of computerized flow parameters with the at least one clinically measured flow parameter.

19. A system for generating a geometric model of a native heart valve, the system comprising at least one computer system configured to:
  receive patient-specific imaging data of the native heart valve and inflow and outflow tracts of the native heart valve;
  receive at least one patient-specific clinically measured flow parameter related to blood flow through the native heart valve and the inflow and outflow tracts;
  generate a first rigid-walled geometric model of the heart valve and the inflow and outflow tracts at a single point in time, based at least partially on the imaging data, the rigid-walled geometric model having modeling parameters and model boundaries representing physical features of an anatomic topology of the native heart valve and inflow and outflow tracts at the single point in time;
  model blood flow through the first rigid-walled geometric model to generate a first set of computerized flow parameters, wherein generating the first set of computerized flow parameters comprises applying boundary conditions, corresponding to desired flow, to a portion of the rigid-walled geometric model that contains the native heart valve and the inflow and outflow tracts, and wherein applying the boundary conditions comprises selecting boundary conditions based at least partially on patient-specific clinical measurements;
  compare the first set of computerized flow parameters with clinically measured flow parameters;
  adjust at least one of the modeling parameters of the first geometric model, based on the comparison of the first set of computerized flow parameters with the clinically measured flow parameters, to generate a second rigid-walled geometric model, wherein the at least one of the modeling parameters comprises at least one of the physical features;

model blood flow through the second rigid-walled geometric model to generate a second set of computerized flow parameters that agrees more closely with the at least one clinically measured flow parameter than the first set of computerized flow parameters agrees with the at least one clinically measured flow parameter, the closer agreement indicating a more accurate rigid-walled geometric model;

compare the second set of computerized flow parameters with the clinically measured flow parameters; and repeat the adjusting, modeling and comparing steps until a desired level of agreement is reached between a most recently calculated set of computerized flow parameters and the at least one clinically measured flow parameter.

20. A system as in claim 19, wherein the at least one computer system is further configured to determine, before the adjusting step and based on the comparison of the first set of parameters with the clinically measured parameters, that the first geometric model is unacceptable.

21. A system as in claim 20, wherein, to determine that the first geometric model is unacceptable, the at least one computer system is configured to determine that the first set of flow parameters differs from the clinically measured flow parameters by at least a predetermined threshold amount.

22. A system as in claim 19, wherein, to generate the first set of computerized flow parameters, the at least one computer system is further configured to:

discretize the first rigid-walled geometric model; and initialize and solve mathematical equations of blood flow through the first rigid-walled geometric model.

23. A method as in claim 19, wherein selecting the boundary conditions comprises selecting inflow and outflow boundary conditions that compensate for at least one underlying psychological condition or medical condition, wherein the at least one underlying psychological condition or medical condition is selected from the group consisting of pain, anxiety, fear, anemia, hyperthyroidism, left ventricular systolic dysfunction, left ventricular hypertrophy, hypertension and arterial-venous fistula.

24. A system as in claim 19, wherein the at least one computer system is further configured to perform at least one of a sensitivity analysis or an uncertainty analysis on at least one of the first set or the second set of computerized flow parameters.

* * * * *